United States Patent

Polzius et al.

[11] Patent Number: 6,130,097
[45] Date of Patent: *Oct. 10, 2000

[54] PROCESS AND DEVICE FOR DETECTING DUST-ASSOCIATED SUBSTANCES

[75] Inventors: Rainer Polzius, Lübeck; Jessica Mahn, Stockelsdorf; Thomas Wuske, Malente, all of Germany

[73] Assignee: Dräger Sicherheitstechnik GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/129,481

[22] Filed: Aug. 4, 1998

[30] Foreign Application Priority Data

Feb. 28, 1998 [DE] Germany ............... 198 08 598

[51] Int. Cl.[7] .................................................. G01N 33/48
[52] U.S. Cl. ........................ 436/169; 436/178; 422/58; 422/61
[58] Field of Search .................... 436/169, 178; 422/83, 86, 88, 69, 70, 58, 61

[56] References Cited

U.S. PATENT DOCUMENTS 4,806,490  2/1989  Bischoff et al. .................... 436/98
4,977,095  12/1990  Zaromb .............................. 436/178

FOREIGN PATENT DOCUMENTS 0 377 229 B1  7/1990  European Pat. Off. .
WO 96/07099  3/1996  WIPO .

*Primary Examiner*—Lyle A. Alexander
*Attorney, Agent, or Firm*—McGlew and Tuttle, P.C.

[57] ABSTRACT

A process for detecting dust-associated substances wherein the dust to be analyzed is brought together with a solvent for eluting the substance to be detected from the dust. The particulate components are retained by means of a filter matrix while the solvent and the substances dissolved and/or suspended therein are transported through the filter matrix by capillary liquid transport. The solvent and the substances dissolved and/or suspended therein are transferred into a reaction matrix adjoining the filter matrix by capillary liquid transport. The substance to be detected is detected in the reaction matrix by means of a chemical and/or biochemical reaction or by the failure of a chemical and/or biochemical reaction to take place. A device for detecting dust-associated substances preferably contains, besides the filter matrix and the reaction matrix, a container for receiving the dust to be analyzed, wherein the container is in liquid connection with the filter matrix.

33 Claims, 2 Drawing Sheets

PROCESS AND DEVICE FOR DETECTING DUST-ASSOCIATED SUBSTANCES

FIELD OF THE INVENTION

The present invention pertains to a process and a device for detecting dust-associated substances.

BACKGROUND OF THE INVENTION

The analysis of dust-associated substances represents an important possibility for evaluating pollution situations and exposure concentrations of certain chemical or biogenic substances, especially in indoor areas. Toxic substances, such as pesticides, polyaromatic hydrocarbons or polychlorinated biphenyls, as well as allergy-inducing biogenic substances, such as allergens of dust mites, epithelia of domestic animals or molds are of particular significance.

According to the current state of the art, the detection of dust-associated substances requires, besides an extraction step, the separation of the particles from extractants and a subsequent, usually complicated laboratory analysis.

For example, the polyaromatic hydrocarbon benzopyrene is determined by collection on a glass fiber filter in the total dust in a recognized analytical method for determining cancer-causing working materials. The quantification of benzopyrene is performed by means of a thin-layer chromatographic or gas chromatographic detection following extraction with a solvent and separation of the particulate components.

The drawback of this process is that the individual working steps are carried out separately and the handling involved in the entire analysis is complicated.

Immunochemical detection methods were developed for the detection of some relevant indoor allergens, e.g., those of mites and cats. The dust-associated allergens are eluted with water after separating the particles. The allergen concentration is subsequently determined separately from the eluate by means of the ELISA method ("Enzyme-Linked Immunosorbent Assay").

A process with which dust-associated allergens are detected based on their enzyme activity is described in EP 0 377 229. The underlying process comprises a complicated sample preparation comprising extraction, dialysis and affinity chromatography, before the detection reaction can be carried out.

A process with which the allergen burden caused by dust mites can be quantified on the basis of the detection of the guanine concentration in house dust is described in U.S. Pat. No. 4,806,490. After a complicated sample preparation, comprising a plurality of extraction and centrifuging steps, the guanine content in the house dust is determined according to a separate colorimetric reaction with aromatic diazo compounds.

A simpler process for determining dust-bound macromolecular analytes is described in WO 96/07099. The device on which this process is based makes it possible to elute dust-associated macromolecules, e.g., allergens, from dust particles collected on a filter. The macromolecules are immobilized in the immediate vicinity of the particles. The immobilized macromolecules can subsequently be detected by means of chemical/biochemical solid-phase reactions. The drawback of this process is that the detection reaction must subsequently be performed as a separate step.

SUMMARY AND OBJECTS OF THE INVENTION

The primary object of the present invention is to provide a possibility for carrying out the detection of dust-associated substances rapidly, reliably and without major expense.

The process according to the present invention consequently takes place essentially such that a) substances eluted from a dust suspension are transported through a filter matrix by capillary liquid transport, b) the particulate components are filtered out by the filter matrix in the process, c) the eluted substances are transported into a next reaction matrix by capillary liquid transport, and d) the substances in the reaction matrix are detected by a chemical or biochemical reaction.

The process according to the present invention makes possible the detection of dust-associated analytes (substances to be detected) in an automatic process, so that the complicated processing of the dust samples known from the state of the art can be abandoned. As a result, it is achieved, in particular, that the analytical system can be used on the site by laymen. This is possible by means of the device according to the present invention by separating the dust particles by a filter matrix (preferably a filter-like mat), which is an integral component of the detection system, and by transporting the substances eluted by means of a solvent into a next zone of the detection system (reaction matrix) by means of capillary liquid transport. The detection of the analyte is performed in the latter zone on the basis of chemical and/or biochemical reactions, preferably as a change in color.

According to the invention a device is provided for detecting dust-associated substances with a filter matrix. The filter matrix is designed to retain particulate components of the dust to be analyzed and to transport a solvent for eluting the substance to be detected from the dust as well as the substances dissolved and/or suspended in the solvent by capillary liquid transport. A reaction matrix is provided which is in fluid connection with the filter matrix. The fluid connection is intended for capillary liquid transport, and has a detection reagent for detecting the substance to be detected.

The device preferably has a container, which is used to receive the dust to be analyzed and is in fluid connection with the filter matrix. The dust-associated analytes can be eluted from the dust sample in the container in a simple manner by adding the solvent in order for the analyte to subsequently enter the filter matrix by capillary liquid transport, by which filter matrix an effective separation from the dust particles is achieved.

Many embodiments of the process according to the present invention and of the device according to the present invention are described herein, especially with respect to the basic reaction steps and the design of the filter matrix and the reaction matrix. The detection system for a certain substance depends, in the particular case, on the properties of that substance. As far as the chemical and/or biochemical reaction process is concerned, the person skilled in the art can select the suitable reaction reagents based on literature already known for the particular case and can design the detection system based on his know-how and the disclosure of this specification in a suitable manner.

In summary, the present invention provides a device and a process that are suitable for the qualitative or even for the quantitative determination of dust-associated substances. The detection of the dust-associated substances is performed in one step from a dust suspension by mechanically separating the dust particles by means of a filter matrix and detecting the dissolved substances in a reaction matrix, which is in contact with the filter matrix. Due to its porous structure, the reaction matrix makes possible the autonomous capillary transport of the soluble substances, whose detection is performed preferably by means of a color reaction as a consequence of the solubilization of chemical or biochemical reagents, which are deposited or immobilized in the filter matrix and in the reaction matrix.

The device according to the present invention and the process according to the present invention for detecting dust-associated substances will be described in greater detail below on the basis of exemplary embodiments.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
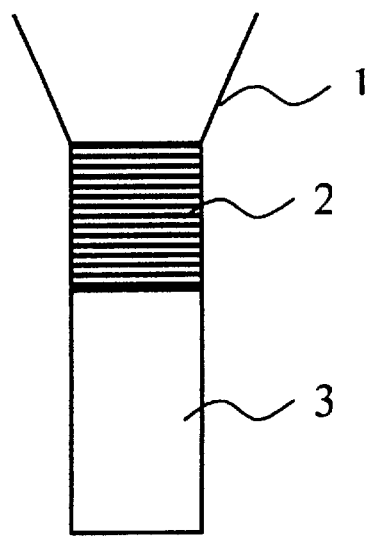
FIG. 1a is a schematic cross-sectional view of a first embodiment of a device for detecting dust-associated substances.
Figure 1B:
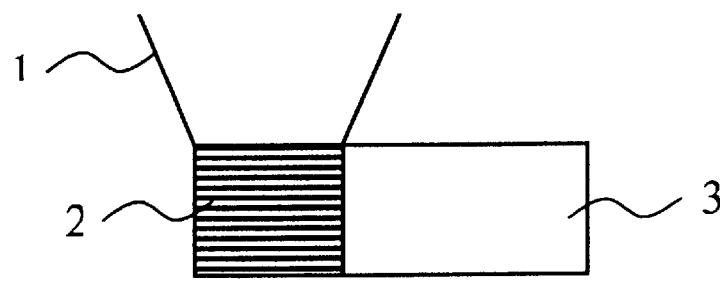
FIG. 1b is a schematic cross-sectional view of a second embodiment of a device for detecting dust-associated substances.

Referring to the drawings in particular, the device according to FIG. 1a and according to FIG. 1b comprises a container 1, which is used to receive the dust or a dust suspension to be analyzed, a filter matrix 2, which forms the bottom of the container 1, and a reaction matrix 3, which is able to build up a fluid contact with the filter matrix 2. The filter matrix 2 and the reaction matrix 3 have separate individual discrete areas which are not intermixed, as shown in the drawings by the separate structures representing the filter matrix 2 and the reaction matrix 3. The components may be arranged such that a vertical (FIG. 1a) or lateral (FIG. 1b) liquid transport is achieved between the filter matrix 2 and the reaction matrix 3.

The container 1 has the task of accommodating a certain volume of the dust to be analyzed or of a suspension of the dust to be analyzed, which is typically 0.05 mL to 5 mL. Various plastics or metals, which are tight and resistant with respect to aqueous and organic solvents, may be used as materials for the container 1.

The bottom of the container 1 is formed by a filter matrix 2, which may be designed as a membrane or mat and may consist of, e.g., glass fibers, cellulose, plastics or silica. To also obtain a capillary-active function, besides the filter function, materials whose pore diameter is between 0.1 $\mu$m and 50 $\mu$m and that have a rate of linear water uptake (linear velocity of flow of the liquid absorbed) of 1 mm/minute to 10 cm/minute are preferably used for the filter matrix 2). Materials characterized by a pore diameter between 0.5 $\mu$m and 10 $\mu$m and a rate of linear water uptake of 5 mm/minute to 5 cm/minute are especially preferred. The thickness of the material may vary from 100 $\mu$m to 0.5 cm.

All types of materials which establish a fluid contact with the upstream filter matrix 2 after the application of a dust suspension and are characterized by the substance to be detected, which is dissolved in the elution liquid (solvent), being bound to the matrix to a low extent at best, may be used as materials for the reaction matrix 3. The reaction matrix 3 may consist of only one material or a plurality of different materials, which make possible a fluid contact with one another. Especially preferred are membranes or mats that have a thickness between 25 $\mu$m and 0.5 cm and whose pore diameter is between 0.1 $\mu$m and 50 $\mu$m and have a rate of linear water uptake between 1 mm/minute and 10 cm/minute. Membranes or mats that make possible the immobilization of detection reagents via adsorptive or covalent bonds, e.g., nitrocellulose or activated nylon membranes, are also preferred.

Figure 2:
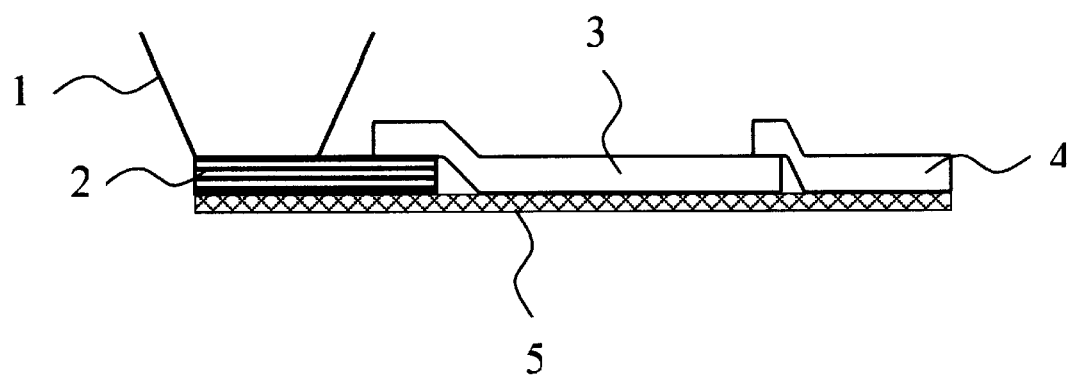
FIG. 2 is a schematic cross-sectional view of a filter matrix and a reaction matrix in overlapping arrangement.

The filter matrix 2 and the reaction matrix 3 may be made in one piece with one another. However, they may also be two separate parts, which adjoin one another. To guarantee a capillary liquid transport from the filter matrix 2 into the reaction matrix 3 in this case, the filter matrix 2 and the reaction matrix 3 may be arranged, e.g., in an overlapping arrangement. It is also conceivable that the filter matrix 2 and/or the reaction matrix 3 is made up of multiple parts each in itself, i.e., they may have two or more than two parts. For example, adjoining parts may overlap each other as shown in FIG. 2. For example, a first part of the filter matrix 2 may adjoin a matrix that contains a labeled reagent (see below) and also has a filter effect. This matrix adjoins, e.g., the reaction matrix 3, which contains, e.g., an immobilized binding partner (see below). It may be advantageous for the reaction matrix 3 to be in fluid contact with a liquid-absorbing matrix 4, e.g., with a mat 4, which overlaps the reaction matrix 3 and whose purpose it is to absorb excess solvent. These various elements may be provided on a support 5 as shown in FIG. 2.

The substance to be detected may be detected in the reaction matrix 3 preferably visually as a change in color by a chemical or biochemical reaction. The reagents needed for this, which may be chemicals such as pH indicators, or biological reagents, e.g., enzymes or specific antibodies, are deposited or immobilized in the dried form in the reaction matrix 3. Deposited reagents are resolubilized by the elution liquid and thus they can react with the analyte. In the case of immobilization of the detection reagents, a chemical or biochemical solid-phase reaction takes place. However, the detection may also take place via a homogeneous reaction in the liquid phase.

Biochemical solid-phase reactions that are based on the antibody-antigen interaction are especially preferred. Such processes have been known to the person skilled in the art as immunochromatography or as immunoconcentration (Price and Newman, 1991, *Principles and Practice of Immunoassay*, Stockton Press, 563–609). A specific binding partner is immobilized in this case in the reaction matrix 3. The coupling with the solid phase may be performed adsorptively, ionically, covalently or by bridging the specific binding partner with, e.g., protein A, avidin or latex particles. Depending on the format of the immunochemical detection, the solid-phase reaction consists of the formation (a) of a complex of the immobilized binding partner, the substance to be detected and a labeled binding partner (two-sided test) or (b) of a complex of the immobilized binding partner and a labeled binding partner, whose binding properties are influenced by binding to the substance to be detected (competitive test).

Antibodies, which may be monoclonal or polyclonal, or fragments thereof are preferably used as binding partners. The substance to be detected or derivatives of the substance to be detected, which may be coupled with macromolecules, are used as binding partners in the competitive test, besides the specific antibodies. Embodiments in which the labeled binding partner is bound by a trapping zone and the labeled binding partners which break through and are not held by the trapping zone by binding to the substance to be detected are preferred in the case of the competitive test. This principle has been known from thin-layer chromatography (C. R. Lowe and P. D. G. Dean, *Affinity Chromatography*, Wiley & Sons, New York, 1974) and is the basis of, e.g., EP 0 052 769. Detailed examples of a two-sided test and of a competitive test are described below.

The labeled binding partners may be contained in the dry form in the filter matrix 2 or in the reaction matrix 3. The labeled binding partners are dissolved from the matrix as a consequence of the liquid transport of the elution liquid and are transported into the zone in which the immunochemical solid-phase reaction takes place.

Enzymes, fluorophores, radioactive isotopes or colored particles may be used as labeling substances, i.e., signal-generating components. The use of direct optical labels, such as metal colloids, colored latex particles or fluorophores, is especially suitable for the process.

Examples of substances to be detected in house dust are environmental pollutants, e.g., polyaromatic hydrocarbons, polychlorinated biphenyls and pesticides. However, biogenic pollutants, such as house dust mite allergens, domestic animal allergens, molds, bacteria, viruses, nucleic acids and endotoxins are of special interest.

The device for detecting dust-associated substances may preferably be used in two different ways. In the first case, an aqueous dust suspension, which was prepared in a preceding preparatory step, is applied to the device. This may also be done by bringing the container 1 containing the dust suspension into contact with the filter matrix 2 and with the reaction matrix 3 such that a capillary effect develops via the filter matrix 2 and the filtration and detection reaction described can take place.

In the second case, the container 1 is filled with a defined amount of dust, which is typically between 5 mg and 100 mg, so that the filter matrix 2 is covered by a layer of dust. The extraction and detection reaction is subsequently started by adding elution liquid (solvent), whose volume is typically between 0.05 mL and 5 mL. It was surprisingly found in this connection that a hydrophobic barrier is formed due to the physicochemical properties of house dust, so that the elution liquid (eluent) penetrates into the dust layer only slowly. The consequence of this column effect is that the residence time of the eluent in the dust phase is prolonged and a high efficiency of extraction is achieved as a result.

Buffered aqueous solutions with a pH value between 4 and 12, which may contain up to 50 vol. % of organic solvents, are preferably used as eluents. Ionic and nonionic detergents may also be present in the eluent in amounts between 0.01 vol. % and 10 vol. %.

The present invention will be described below in examples on the basis of the detection of pentachlorophenol and of the cat allergen Fel d I from house dust.

EXAMPLE 1

Detection of Pentachlorophenol (PCP) from Dust (Competitive Test)

Principle: The filter matrix contains a PCP-specific binding partner labeled with colloidal gold (gold labeling conjugate). If PCP is present in the elution liquid, this binding partner cannot be trapped by a binding partner (PCP conjugate) present in the immobilized state in the reaction matrix because of its high affinity for PCP, which trapping would occur in the absence of PCP.

a) Preparation of the Gold Label 0.5 L of distilled and filtered (0.2 $\mu$m) water was heated to boiling in a siliconized beaker while stirring and 5 mL of 1% auric acid were added. The solution was boiled for another 5 minutes, and 20 mL of a 1% sodium citrate solution were then rapidly added. A change in color from blue to red indicated the end of the reaction after another 10 minutes. The colloid was cooled to room temperature in an ice bath and stabilized by adding 5 mL of a 2% $NaN_3$ solution and 0.5 mL of 1% PEG (polyethylene glycol) 20000.

b) Preparation of the Gold Label Conjugate

The pH value of the gold colloid solution was adjusted to pH 9 by adding 0.2 M of $K_2CO_3$. Ten mg of a PCP-specific monoclonal antibody were added to the solution and incubated for 30 minutes at room temperature. After adding 200 mg of Crotein C to the solution and incubation for another 30 minutes, the conjugates of antibodies and gold labels were obtained by centrifuging for 15 minutes at 40,000 g, taking up the pellet in 0.1 M of HEPES (hydroxyethyl piperazine ethanesulfonic acid) buffer, pH 7.0, with the additives 0.1% of Crotein C and 0.05% of PEG 20000.

c) Preparation of the PCP Conjugate

One mg of 5-(4-hydroxy-2,3,5,6-tetrachlorophenoxy)-valeric acid was dissolved, together with 1.7 mg of N-hydroxysuccinimide (NHS) and 6.2 mg of N,N'-dicyclohexylcarbodiimide (DCC), in DMF and incubated at room temperature for 18 hours. The mixture was subsequently added dropwise to a solution of 2 mg of goat IgG in 2 mL of a 0.15-M sodium hydrogen carbonate solution, incubated for another 3 hours, and dialyzed for 2 days against PBS buffer.

d) Preparation of the Filter Matrix

GF/F glass fiber mat (Whatman, U. K.) was cut into strips with a width of 0.8 cm and a length of 2.5 cm, impregnated in the gold label conjugate solution (optical density at 520 nm adjusted to 2) and dried at 40° C. for 20 minutes in a forced-air oven.

e) Building up of the Reaction Matrix

A nitrocellulose membrane with a pore size of 5 $\mu$m (Schleicher & Schüll, Germany), which had a width of 0.8 cm and a length of 5 cm, was fixed as the reaction matrix on a plastic laminate with a thickness of 1 mm by means of a two-sided adhesive tape. The PCP conjugate was sprayed on as a line at a concentration of 5 mg/mL (1 $\mu$L/cm) at a distance of 1 cm from the front edge of the nitrocellulose by means of a Camag Linomat IV (Camag, Switzerland). The membrane was subsequently dried in a forced-air oven for 30 minutes at 40° C., blocked with a 0.1% bovine serum albumin solution for 10 minutes, and dried again for 30 minutes at 40° C.

f) Assembly of the Analytical System

The filter matrix impregnated with gold label conjugate was fixed with two-sided adhesive tape on the plastic laminate such that it overlapped the reaction matrix by 2 mm at its front end. A test strip with a width of 0.8 cm, which consisted of a filter matrix of a length of 2.5 cm and, adjoining it, of a reaction zone with a length of 5 cm, and whose individual components were in fluid contact with one another, was thus obtained.

g) Analysis of Dust Samples

Fifty mg of house dust in 1 mL of elution liquid (0.1-M phosphate buffer, pH 8.0, 25% methanol, 0.05% Triton 100) were extracted by shaking for 5 minutes in a container (diameter: 1 cm, height: 2 cm).

The detection reaction for PCP was subsequently started by placing the analytical system (f) vertically into the container, wherein the filter matrix dipped into the dust suspension. In the case of an uncontaminated dust sample, a red line developed in the reaction matrix after about 5 minutes. The red line was not visible in the presence of PCP in amounts of at least 1 $\mu$g/g.

EXAMPLE 2

Detection of the Cat Allergen Fel d I from Dust (Two-sided Test)

Principle: The filter matrix contains a Fel d I-specific binding partner labeled with colloidal gold (gold label conjugate). A second binding partner, which is specific of Fel d I and becomes visible in the case of the presence of Fel d I due to Fel d I-mediated binding of the gold label conjugate, is immobilized in the reaction matrix.

a) Preparation of the Gold Label 0.5 L of distilled and filtered (0.2 $\mu$m) water was heated to boiling in a siliconized beaker while stirring and 5 mL of a 1% auric acid were added. The solution was boiled for another 5 minutes, and 20 mL of a 1% sodium citrate solution were then rapidly added. A change in color from blue to red indicated the end of the reaction after another 10 minutes. The colloid was cooled to room temperature in an ice bath and stabilized by adding 5 mL of a 2% $NaN_3$ solution and 0.5 mL of 1% PEG (polyethylene glycol) 20000.

b) Preparation of the Gold Label Conjugate

The pH value of the gold colloid solution was adjusted to pH 9 by adding 0.2 M $K_2CO_3$. Ten mg of a first, Fel d I-specific monoclonal antibody were added to the solution and incubated at room temperature for 30 minutes. After adding 200 mg of RSA to the solution and incubation for another 30 minutes, the conjugates of antibodies and gold labels were obtained by centrifuging for 15 minutes at 40,000 g, taking up the pellet in 0.1 M of HEPES (hydroxyethyl piperazine ethanesulfonic acid) buffer, pH 7.0, with 0.1% of RSA and 0.05% of PEG 20000 as additives.

c) Preparation of the Filter Matrix

Glass fiber mat material F075-14 (Whatman, U. K.) was cut into strips with a width of 0.8 cm and a length of 2.5 cm, impregnated in the gold label conjugate solution (optical density at 520 nm adjusted to 3) and dried at 40° C. for 20 minutes in a forced-air oven.

d) Building up the Reaction Matrix

A nitrocellulose matrix with a pore size of 5 $\mu$m (Schleicher & Schüll, Germany), which had a width of 0.8 cm and a length of 2.5 cm, was fixed as the reaction matrix on a plastic laminate by means of a two-sided adhesive tape. A second Fel d I-specific monoclonal antibody was sprayed on as a line at a concentration of 1 mg/mL (1 $\mu$L/cm) at a distance of 1 cm from the front edge of the nitrocellulose by means of a Camag Linomat IV (Camag, Switzerland). The membrane was subsequently dried for 30 minutes at 40° C. in a forced-air oven, blocked with a 0.1% bovine serum albumin solution for 10 minutes, and dried again for 30 minutes at 40° C.

e) Assembly of the Analytical System

The filter matrix impregnated with gold label conjugate was fixed on the plastic laminate with two-sided adhesive tape such that it overlapped the reaction matrix by 2 mm at its front end. A glass fiber mat GF/F (Whatman, U. K.) having a length of 2 cm and a width of 0.8 cm, which was used as the liquid absorption matrix, was fixed at the rear end of the reaction matrix, likewise with an overlap of 2 mm. A test strip with a width of 0.8 cm, which consisted of a filter matrix with a length of 2.5 cm and, adjoining it, a reaction matrix with a length of 2.5 cm and a liquid absorption matrix with a length of 2 cm, and whose individual components were in fluid contact with one another, was thus obtained.

A polyethylene sleeve with an internal diameter of 0.5 cm and a height of 1 cm was pressed onto the filter matrix of the analytical system and was fixed with an adhesive strip.

f) Analysis of Dust Samples

Thirty mg of house dust, which was contaminated with 10 $\mu$g of Fel d I per g of dust, was filled into the container formed by pressing on the sleeve. The detection reaction was started by adding 0.3 mL of elution liquid (0.1 M of phosphate buffer, pH 8.0, 0.1% of Tween 20). A red line became visible in the reaction matrix after about 5 minutes. No change in color was seen in the reaction matrix in the case of uncontaminated dust samples.

While specific embodiments of the invention have been shown and described in detail to illustrate the application of the principles of the invention, it will be understood that the invention may be embodied otherwise without departing from such principles.

What is claimed is:

1. A process for detecting a substance associated with dust, the process comprising the steps:

bringing together the dust to be analyzed with a solvent to elute the substance to be detected from the dust;

using a filter matrix for retention of the particulate components;

transporting the solvent and the substances dissolved and/or suspended therein through the filter matrix by capillary liquid transport;

transferring the solvent and the substances dissolved and/or suspended therein into a reaction matrix adjoining the filter matrix by capillary liquid transport, said reaction matrix and said filter matrix having separate individual discrete areas which are not intermixed, said reaction matrix and said filter matrix adjoining each other in a fluid capillary connection;

detecting the substance to be detected in the reaction matrix by means of a chemical and/or biochemical solid-phase reaction or by the failure of a chemical and/or biochemical reaction to take place.

2. The process in accordance with claim 1, wherein said chemical and/or biochemical solid-phase reaction takes place with an immobilized detection reagent in the reaction matrix in the presence of the substance to be detected.

3. The process in accordance with claim 1, wherein an antibody-antigen reaction is used.

4. The process in accordance with claim 1, wherein the substance to be detected is detected by means of a color change reaction.

5. The process in accordance with claim 1, wherein the dust to be analyzed is brought together with the solvent in a container that is in fluid connection with the filter matrix, said fluid connection of said container with said filter matrix being spaced from said fluid connection between said filter matrix and said reaction matrix.

6. The process in accordance with claim 1, wherein:

substantially completely transporting the solvent and the substances dissolved and/or suspended therein through said filter matrix from one side of said filter matrix to an opposite side of said filter matrix and into said reaction matrix.

7. The process in accordance with claim 1, wherein the substance to be detected or a reaction product of the substance to be detected reacts with a reagent contained in the reaction matrix to form a product, which is transferred in the reaction matrix by capillary liquid transport.

8. The process in accordance with claim 7, wherein a chemical and/or biochemical solid-phase reaction takes place with an immobilized detection reagent in the reaction matrix in the presence of the substance to be detected.

9. The process in accordance with claim 1, wherein the substance to be detected reacts with a reagent contained in the filter matrix to form a product, said product being transferred into the reaction matrix by means of capillary liquid transport.

10. The process in accordance with claim 9, wherein a reagent labeled with a labeling substance is used as the reagent contained in the filter matrix or in the reaction matrix.

11. The process in accordance with claim 10, wherein an enzyme and/or a fluorophore and/or a radioactive isotope and/or colored particles, preferably colloidal gold, are used as the labeling substance.

12. A device for detecting dust-associated substances, the device comprising:
   a filter matrix, which is designed to retain particulate components of the dust to be analyzed and to transport a solvent for eluting the substance to be detected from the dust as well as the substances dissolved and/or suspended in the solvent by capillary liquid transport through the filter matrix; and
   a reaction matrix being positioned in fluid connection with said filter matrix for receiving the solvent and the substances dissolved and/or suspended in the solvent via the capillary liquid transport through said filter matrix, said reaction matrix having a detection reagent for detecting the substance to be detected, said reaction matrix and said filter matrix being positioned in separate individual discrete adjoining areas which are not intermixed, said reaction matrix and said filter matrix adjoining each other in said fluid connection.

13. The device in accordance with claim 12, wherein said filter matrix and said reaction matrix are made in one piece with one another.

14. The device in accordance with claim 12, wherein said reaction matrix is joined by a liquid absorption matrix.

15. The device in accordance with claim 12, wherein said filter matrix and said reaction matrix comprises a membrane and/or a mat.

16. The device in accordance with claim 12, wherein said filter matrix comprises glass fibers, cellulose, plastics and/or silica.

17. The device in accordance with claim 12, wherein said filter matrix has a thickness in the range of 0.1 mm to 5 mm.

18. The device in accordance with claim 12, wherein said reaction matrix comprises nitrocellulose and/or an activated nylon membrane.

19. The device in accordance with claim 12, wherein said filter matrix and said reaction matrix includes pores with a pore diameter in the range of 0.1 $\mu$m to 50 $\mu$m.

20. The device in accordance with claim 12, wherein said reaction matrix has a thickness in the range of 0.025 mm to 5 mm.

21. The device in accordance with claim 12, wherein said reaction matrix contains a reagent that is designed to react with the substance to be detected or with a reaction product of the substance to be detected to form a product that can be transferred in said reaction matrix by capillary liquid transport.

22. The device in accordance with claim 12, wherein said reaction matrix has an immobilized detection reagent.

23. The device in accordance with claim 12, wherein: a solid-phase reaction takes place with said detection agent to detect the substances.

24. The device in accordance with claim 12, wherein:
   said filter matrix substantially completely transports the solvent and the substances dissolved and/or suspended therein through said filter matrix from one side of said filter matrix to an opposite side of said filter matrix, and into said reaction matrix.

25. The device in accordance with claim 12, wherein said filter matrix contains a reagent that is designed to react with the substance to be detected to form a product that can be transferred into said reaction matrix by capillary liquid transport.

26. The device in accordance with claim 25, wherein the reagent contained in said filter matrix or in said reaction matrix is labeled with a labeling substance.

27. The device in accordance with claim 26, wherein said labeling substance has an enzyme and/or a fluorophore and/or a radioactive isotope and/or colored particles, preferably gold.

28. The device in accordance with claim 12, wherein said filter matrix and said reaction matrix are two separate parts, which adjoin one another.

29. The device in accordance with claim 28, wherein said filter matrix and said reaction matrix are in an overlapped arrangement.

30. The device in accordance with claim 28, wherein said filter matrix is a multipart filter matrix and/or said reaction matrix is a multipart reaction matrix.

31. The device in accordance with claim 12, further comprising a container for receiving the dust to be analyzed in fluid connection with said filter matrix.

32. The device in accordance with claim 31, wherein the bottom or part of the bottom of said container is formed by said filter matrix.

33. The device in accordance with claim 31, wherein said container has an opening on its top side.

* * * * *